US010807922B2

(12) United States Patent
Kardash et al.

(10) Patent No.: US 10,807,922 B2
(45) Date of Patent: Oct. 20, 2020

(54) METHOD OF OLIGOMERIZATION OF OLEFINS

(71) Applicant: PUBLIC JOINT STOCK COMPANY "SIBUR HOLDING", Tobolsk (RU)

(72) Inventors: Vladislav Alexandrovich Kardash, Tomskaya obl. (RU); Denis Alekseevich Lenev, Moskovskaya obl. (RU); Maxim Vladimirovich Lipskikh, Tomsk (RU); Rafael Acevedo Forero, Tomsk (RU)

(73) Assignee: PUBLIC JOINT STOCK COMPANY "SIBUR HOLDING", Region Tobolsk (RU)

( * ) Notice: Subject to any disclaimer, the term of this patent is extended or adjusted under 35 U.S.C. 154(b) by 19 days.

(21) Appl. No.: 16/317,961

(22) PCT Filed: Jul. 15, 2016

(86) PCT No.: PCT/RU2016/000443
§ 371 (c)(1),
(2) Date: Jan. 15, 2019

(87) PCT Pub. No.: WO2018/012997
PCT Pub. Date: Jan. 18, 2018

(65) Prior Publication Data
US 2019/0144357 A1 May 16, 2019

(51) Int. Cl.
| | |
|---|---|
| *C07C 2/36* | (2006.01) |
| *C07C 11/02* | (2006.01) |
| *C07C 2/24* | (2006.01) |
| *C07C 2/32* | (2006.01) |
| *B01J 31/18* | (2006.01) |
| *B01J 23/06* | (2006.01) |
| *B01J 31/12* | (2006.01) |
| *B01J 31/14* | (2006.01) |
| *B01J 31/24* | (2006.01) |
| *B01J 35/00* | (2006.01) |
| *B01J 37/02* | (2006.01) |
| *B01J 37/03* | (2006.01) |
| *B01J 37/04* | (2006.01) |
| *C07C 11/107* | (2006.01) |

(52) U.S. Cl.
CPC .......... *C07C 2/36* (2013.01); *B01J 23/06* (2013.01); *B01J 31/122* (2013.01); *B01J 31/128* (2013.01); *B01J 31/143* (2013.01); *B01J 31/188* (2013.01); *B01J 31/2414* (2013.01); *B01J 35/0006* (2013.01); *B01J 37/0236* (2013.01); *B01J 37/031* (2013.01); *B01J 37/04* (2013.01); *C07C 2/24* (2013.01); *C07C 2/32* (2013.01); *C07C 11/02* (2013.01); *C07C 11/107* (2013.01); *B01J 2231/20* (2013.01); *B01J 2531/62* (2013.01); *B01J 2531/90* (2013.01); *C07C 2531/14* (2013.01); *C07C 2531/24* (2013.01); *C07C 2531/34* (2013.01)

(58) Field of Classification Search
None
See application file for complete search history.

(56) References Cited

U.S. PATENT DOCUMENTS

| | | | |
|---|---|---|---|
| 7,550,639 B2 | 6/2009 | Nabika | |
| 7,906,681 B2 | 3/2011 | Gao | |
| 8,461,406 B2 | 6/2013 | Overett | |
| 8,859,696 B2 | 10/2014 | Hanton | |
| 9,884,793 B2 * | 2/2018 | O'Hare | B01J 31/2295 |

(Continued)

FOREIGN PATENT DOCUMENTS

| | | |
|---|---|---|
| EP | 2832445 A1 | 2/2015 |
| WO | 2004/056479 A1 | 7/2004 |
| WO | 2006/108467 A1 | 10/2006 |
| WO | 2014/181250 A1 | 11/2014 |

OTHER PUBLICATIONS

International Search Report and Written Opinion dated Mar. 30, 2017, directed to International Application No. PCT/RU2016/000443; 5 pages.

Malpass, D.B. (2010) "Commercially Available Metal Alkyls and Their Use in Polyolefin Catalysts," in: Handbook of Transition Metal Polymerization Catalysts, R. Hoff and R.T. Mathers ed., John Wiley & Sons, Inc., pp. 13-14.

Wohl, A. et.al. (2009) "Reaction kinetics of the ethene tetramerization catalyst system CrCl3(THF)3,Ph2PN(iPr)PPh2 and MAO: The unexpected and unusual formation of odd-numbered 1-olefins", Journal of Molecular Catalysis A: Chemical 297: 1-8.

*Primary Examiner* — Tam M Nguyen
(74) *Attorney, Agent, or Firm* — Morrison & Foerster LLP

(57) ABSTRACT

The present invention relates to a method of preparing α-olefins by oligomerization of $C_2$-$C_4$ olefins. The method is carried out by oligomerization of $C_2$-$C_4$ olefins in the presence of a catalyst system comprising a transition metal source, an activator, which is an alkylaluminoxane, and a compound of formula (I), $Ar^1Ar^2P$—$N(R)$—$PAr^3Ar^4$ [formula I], wherein $Ar^{1-4}$ are the same or different and are selected from substituted or unsubstituted $C_6$-$C_{10}$ aryl, R is selected from linear or branched $C_1$-$C_4$ alkyl, substituted or unsubstituted $C_6$-$C_{10}$ aryl, and substituted or unsubstituted $C_3$-$C_{10}$ cycloalkyl, wherein the oligomerization is carried out in a solvent, which is a bicyclic compound or a mixture of bicyclic compounds, preferably decalin. The claimed method provides a significant increase in the activity of the catalyst during the oligomerization process and, as a consequence, a reduction in the catalyst unit consumption, as well a reduction in the formation of polymer by-product.

41 Claims, 1 Drawing Sheet

(56) References Cited

U.S. PATENT DOCUMENTS

| | | |
|---|---|---|
| 2005/0256357 A1* | 11/2005 | Mihan .................. C07C 2/32 585/527 |
| 2007/0156003 A1 | 7/2007 | Furukawa |
| 2010/0137669 A1* | 6/2010 | Han .................. C07C 2/34 585/514 |
| 2012/0316303 A1 | 12/2012 | Hanton et al. |
| 2015/0080629 A1 | 3/2015 | Overett |
| 2015/0361192 A1* | 12/2015 | Lynn .................. C08F 210/16 526/170 |
| 2018/0071725 A1* | 3/2018 | Klosin .................. C07F 9/6568 |
| 2019/0092709 A1* | 3/2019 | Bischof .................. B01J 31/189 |
| 2019/0352439 A1* | 11/2019 | Xu .................. C08F 210/16 |

* cited by examiner

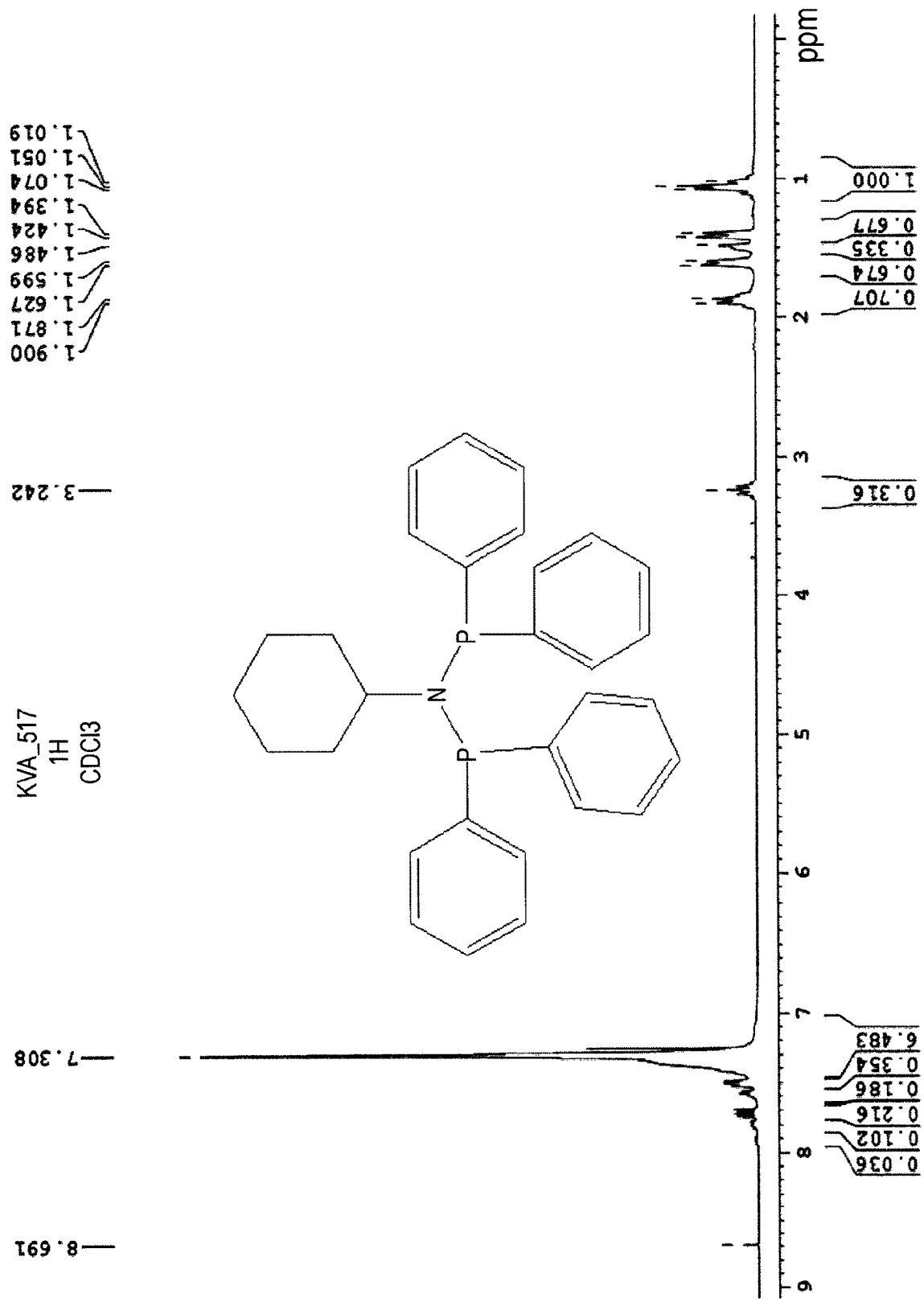

METHOD OF OLIGOMERIZATION OF OLEFINS

REFERENCE TO RELATED APPLICATIONS

This application is a national stage application under 35 USC 371 of International Application No. PCT/RU2016/000443 filed Jul. 15, 2016, the entire contents of which are incorporated herein by reference.

FIELD OF THE INVENTION

The invention relates to the field of oligomerization of olefins to prepare α-olefins, in particular octene-1 used for the manufacture of premium-grade linear low-density polyethylene, poly-alpha-olefins for drag reducing agents and plastomers, and to prepare hexene-1 used for the manufacture of linear low- and high-density polyethylene, polyhexene, etc.

BACKGROUND OF THE INVENTION

A method of oligomerization of ethylene is disclosed in U.S. Pat. No. 7,550,639 (published on 23 Jun. 2009, "Sumitomo Chemical Company, Limited [JP]") in toluene in the presence of a catalyst system comprising a chromium source, a ligand of the general formula: $(Ph^1)(Ph^2)P$—N$(R^2)$—P'$(Ph^3)(Ph^4)$, wherein $Ph^{1-4}$ are preferably phenyl, 2-tolyl, 2-ethylphenyl, 2-isopropylphenyl, 2-phenylphenyl, 2-methoxyphenyl, etc.; $R^2$ may be a hydrogen atom or a hydrocarbyl group, preferably methyl, ethyl, isopropyl or phenyl. An activator is a mixture of an organoaluminum compound, namely methylaluminoxane (MAO) with trioctylaluminum. The document teaches that the addition of an additional aluminum compound improves the efficiency of the system in terms of oligomers. Said method provides a product comprising up to 14.4 wt. % and 46 wt. % of hexene-1 and octene-1, respectively (Example 4). An obvious disadvantage of the invention is the formation of polyethylene in an amount of 27% based on liquid oligomers (Example 4), accompanying a significant amount of octene-1.

A known method of oligomerization of ethylene is carried out in the presence of a catalyst system comprising a chromium compound and a ligand of the general formula: $R_1R_2P$—$N(R_3)$—$P(R_4)$—$NR_5R_6$ or $R_1R_2P$—$N(R_3)$—$P(XR_7)_2$, wherein $R_1$, $R_2$, $R_3$, $R_4$, $R_5$, $R_6$, and $R_7$ are independently $C_1$-$C_{10}$ alkyl, $C_6$-$C_{20}$ aryl, $C_3$-$C_{10}$ cycloalkyl, aralkyl, alkylaryl, or trialkylsilyl, most preferably, methyl, ethyl, isopropyl, tert-butyl, cyclohexyl, phenyl, etc., or cyclic derivatives of said ligands, wherein at least one P or N in the PNPN or PNP structures is a part of a ring system, and X is an oxygen or sulfur atom (European application EP 2832445 published on 4 Feb. 2015, "Linde AG [DE]" and "Saudi Basic Industries Corporation [SA]"). A catalyst activator or co-catalyst is trimethylaluminum, triethylaluminum, MAO, modified MAO (MMAO), or the like. In specific embodiments, the aluminum content is 7 wt. %. A solvent is an aromatic hydrocarbon (toluene, chlorobenzene). The method provides co-production of hexene-1 and octene-1, and a high selectivity and catalyst activity. A disadvantage of the method is the necessity of using an asymmetric PNPN-ligand and a modified methylaluminoxane (MMAO), which are synthesized by complex and multistep procedures. In one embodiment of the invention (Example 3), the method is carried out in the presence of an unmodified MAO used in the form of a 10% solution in toluene. However, the obtained results show that the use of MAO preferably results in the formation of hexene-1, i.e. the trimerization process is predominant. In addition, the selectivity to α-olefins in terms of the total amount of the resulting $C_6$ and $C_8$ olefins is low. Thus, in Example 3, their content in the product was 45.8 and 37.6 wt. %, respectively. Selectivity to $C_6$-1 and $C_8$-1 was 92.6 and 99.1%, respectively. Furthermore, in addition to $C_6$ and $C_8$ olefins, there is a large amount of $C_{10+}$ oligomers (15.7 wt. %). In example C*, MAO is also used in the form of a 10% solution in toluene, and the solvent is chlorobenzene. This experiment shows the formation of a large amount of octenes relative to hexenes (46.5 and 36.4 wt. %, respectively), but the selectivity to hexene-1 and octene-1 is low (86.2 and 99%, respectively). In addition, it should be noted a formation of a large amount of $C_{10+}$ oligomers (15.6 wt. %) and a large amount of a polymer by-product (7 g based on the total weight of all products (80 g)).

Another method of oligomerization of ethylene is carried out in the presence of a catalyst comprising a chromium source; a ligand of the general formula: $(Ph_1)(Ph_2)P$—N$(R_2)$—P'$(Ph_3)(Ph_4)$, wherein $Ph_{1-4}$ are phenyl groups, wherein at least one of the $Ph_{1-4}$ substituents is substituted in the ortho-position with a halogen atom or do not have a substituent in the ortho-position, and $R_2$ is a hydrogen atom, a $C_1$-$C_{20}$ hydrocarbon substituent, or silyl; and an activator (MAO) (U.S. Pat. No. 7,906,681, published on 15 Mar. 2011, "Nova Chemicals (International) S.A. [CM]"). The solvent is toluene. The method provides an ethylene conversion of 80% and a high selectivity to hexene-1 and octene-1. However, it requires an expensive and hardly available diphosphine ligand with fluorine atoms in four phenyl substituents.

Another known method of tetramerization of ethylene is carried out in the presence of a catalyst comprising a chromium source, a ligand of the general formula: $(R^1)_m$AXY, and an activator, which is an organoaluminum compound and/or organoboron compound (preferably MMAO is used) (WO 2014/181250 published on 13 Nov. 2014, "Sasol Technology (Proprietary) Limited [ZA]"). The method is carried out in a solvent at 80-120° C. The ligand $(R^1)_m$AXY is characterized in that its structure contains a phosphorus atom in the phosphorus-containing heterocycle Y, such as phosphol or dibenzophosphol. The new formula of the ligand increases the catalyst stability at elevated temperatures, and allows synthesis in which the formed polyethylene remains in the solution. This allows the process without fouling the reactor, pipes, heat exchangers, and other equipment and without shutdown for cleaning purposes. The method also provides a high content of octene-1 in the product. In specific embodiments, the content of octene-1 reaches 68.1 wt. %. However, said method requires an expensive and hardly available asymmetric diphosphine ligand. Furthermore, it results in the formation of a large amount of $C_{10+}$ oligomers (up to 19.5 wt. %), and as the amount of octene-1 increases, the formation of a polymer by-product also increases (up to 13.6 wt. %).

Another known method is method of tetramerization of ethylene in the presence of an activated catalyst at a temperature of 80-115° C. during a continuous process (application US 2015/0080629, published on 19 Mar. 2015, "Sasol Technology (Proprietary) Limited [ZA]"). The activated catalyst is prepared by mixing a chromium source, a diphosphine ligand of the general formula: $R^1R^2P^1XP^2R^3R^4$, wherein X may be —N(Ar)—N(Ar)— (Ar is aryl), —N(Alk)-N(Alk)- (Alk is alkyl or cycloalkyl), etc.; $R^1$, $R^2$, $R^3$, and $R^4$ are methyl, ethyl, propyl, isopropyl, cyclohexyl, benzyl, phenyl, tolyl, xylyl, cumyl, etc. The catalyst activator is MMAO. The solvent is methylcyclohexane. The process conditions allow the synthesis in which the formed polyethylene remains in the solution. This allows the process without fouling the reactor, pipes, heat exchangers, and other equipment and without shutdown for cleaning purposes. A disadvantage of the method is the use of expensive and hardly available ligands and the modified activator. In addition, the amount of the formed by-product increases depending on an increased amount of the formed octene-1.

Another method of tetramerization of ethylene is carried out in the presence of a catalyst comprising a chromium source, a ligand of the general formula: $(Ar^1)(Ar^2)P$—N(R)—$P'(Ar^3)(Ar^4)$, wherein R is hydrogen, alkyl, substituted alkyl, aryl, substituted aryl, etc., $Ar^{1-4}$ are preferably phenyl or substituted phenyl; and a metal-containing activator. The activator is MMAO (U.S. Pat. No. 8,461,406, published on 11 Jun. 2013, "Sasol Technology (PTY) Limited [ZA]"). After a short pre-activation of the catalyst in the presence of ethylene in reactor 1, said catalyst is further diluted with a solvent in reactor 2 to reduce the concentration of aluminum and chromium, which results in a sharp increase in the specific activity and selectivity to liquid oligomers as opposed to polyethylene. The solvent is selected from aliphatic hydrocarbons that may include cyclic compounds and their derivatives. In specific embodiments, the selectivity to hexene-1 and octene-1 is 15 and 69.3 wt. %, respectively. Disadvantages of the method are an increased metal consumption because the use of two reactors. In addition, a high content of octene-1 in the product is achieved when a modified methylaluminoxane (MMAO) is used and the solvent is methylcyclohexane. The description of the invention also provides examples with MAO and toluene as a solvent, but the content of octene-1 in the product is 0.5 to 8.5 wt. %, i.e. the trimerization process is predominant Another known method of tetramerization of ethylene is carried out in the presence of a catalyst system prepared by mixing a chromium source and a ligand of the general formula: $(Ar^1)(Ar^2)P$—N(R)—$P'(Ar^3)(Ar^4)$, wherein R is a hydrogen atom, a hydrocarbyl group, a heteroatom-containing hydrocarbyl group, or halogen, Ar1-4 are phenyl, tolyl, xylyl, benzyl, cumyl, or the like (U.S. Pat. No. 8,859,696 published on 14 Oct. 2014, "Sasol Technology (PTY) Limited [ZA]"). The catalyst activator is an organoboron compound of the general formula: $[(R)_xL^*\text{-}H]^*[B(R^4)_4]^-$, in combination with a co-activator (trialkylaluminum) or only an organoaluminum compound (modified methylaluminoxane (MMAO), etc.). In addition, the reaction mass is supplemented with a zinc-containing compound, which is a zinc halides, zinc oxygenates, zinc alkyls, or the like, to reduce the amount of the formed polyethylene. A disadvantage of the method is the necessity of using an additional activator and a co-activator of the catalyst system. In addition, the description of the invention fails to indicate the selectivity to octene-1 and hexene-1, but only the total selectivity to octene and hexene.

Furthermore, US20150080629, U.S. Pat. Nos. 8,461,406, and 8,859,696 teach a method comprising the use of a modified methylaluminoxane MMAO soluble in aliphatic solvents, i.e. methylaluminoxane containing $C_2$-$C_{20}$ alkyl, for example, isobutyl or octyl (MMAO-4A and MMAO-12A, Akzo Nobel). However, the methods for preparing MMAO are complex and multistep and requires the use of an additional organoaluminum compound other than trimethylaluminum. Thus, the hydrolytic process for preparing MMAO, for example, requires first the hydrolysis of a long-chain trialkylaluminum, then the addition of trimethylaluminum to the reaction mixture, and after that an additional hydrolysis of the resulting mixture, wherein the procedure must be repeated several times, as disclosed in application EP1352913 (published on 15 Oct. 2003, "Tosoh Finechem Corp. [JP]").

The closest method to the developed one is a method of tetramerization of olefins, as disclosed in application WO2004056479 (published on 8 Jul. 2004, "Sasol Technology (PTY) LTD [ZA]"). The method is carried out in the presence of a catalyst system comprising a chromium source, a ligand of the general formula: $(R^1)(R^2)P$—N($R^5$)—$P(R^3)(R^4)$, wherein $R^{1\text{-}4}$ are independently benzyl, phenyl, tolyl, xylyl, naphthyl, methyl, ethyl, propyl, butyl, or the like, and $R^5$ is hydrogen, alkyl, substituted alkyl, aryl, substituted aryl, halogen, or the like; and an activator, which is MAO. The method provides the tetramer content in the product of 30 wt. % and more.

However, the use of an available unmodified methylaluminoxane has a number of limitations, such as the use only of aromatic solvents because the unmodified MAO is insoluble in aliphatic and cycloaliphatic solvents. In turn, the use of aromatic solvents results in a reduced stability of the catalyst system. Moreover, the products obtained by using the unmodified MAO in an aromatic solvent are of a limited use because aromatic solvents are highly toxic and may exist in trace amounts in the product. WO2004056479 shows that a PNP-MAO-Cr catalyst system is characterized by a high activity (from 20,000 to 500,000 g/g Cr*h) in toluene or cyclohexane (Examples 2, 22). The comparative experiments conducted by the inventors of the claimed invention did not succeed to reproduce the results of Examples 2 and 22 (Table 1, an activity of 600 to 2,700 g/g Cr*h) (see comparative experiments (Examples 5 and 6)). The results obtained in the comparative experiments are also consistent with the data disclosed in the article of Rosenthal et. al. (see Journal of Molecular Catalysis A: Chemical 297 (2009) 1-8). The article also provides a much lower activity for toluene when Cr-PNP-MAO is used (from 1,000 to 2,000 g/g Cr*h). Furthermore, a significant amount of polyethylene slurry (up to 50% of the yield) was found to form in toluene, especially when the used catalyst system has a storage time of 60 minutes or more.

Thus, the known methods of oligomerization of ethylene aimed to co-production of hexene-1 and octene-1 are characterized by the necessity of the use of a catalytic system consisting of a hardly available and expensive ligand and an activators, such as a modified MAO, which are synthesized by a complex and multistep method. At the same time, the use of an unmodified MAO leads to the predominant reaction of trimerization (to form hexene-1) rather than tetramerization (to form octene-1).

In addition, in these methods, as octene-1 increases in the final product, the formation of by-products, such as $C_{10+}$ and/or a polymer, increases.

Thus, there is the need for the development of an effective method of oligomerization of $C_2$-$C_4$ olefins to produce α-olefins, in particular, by concurrent processes of trimerization and tetramerization of ethylene to obtain hexene-1 and octene-1, in the presence of a relatively inexpensive and easily synthesized ligand, such as a symmetric unsubstituted phenylphosphine ligand of the formula: $(Ph_2P)_2NR$ (PNP), and an activator, such as unmodified MAO.

SUMMARY OF THE INVENTION

The present invention provides a method for preparing α-olefins by oligomerization of $C_2$-$C_4$ olefins, namely a method of co-production of hexene-1 and octene-1, characterized by a high efficiency and a lower formation of by-products.

The method for preparing α-olefins is carried out by oligomerization of $C_2$-$C_4$ olefins in the presence of a catalyst system comprising a transition metal source, an activator, which is an alkylaluminoxane, and a compound of formula (I):

$$Ar^1Ar^2P\text{—}N(R)\text{—}PAr^3Ar^4 \quad \text{[formula I]},$$

wherein $Ar^{1-4}$ are the same or different and are selected from substituted and unsubstituted $C_6$-$C_{10}$ aryl groups, R is selected from linear or branched $C_1$-$C_4$ alkyl groups, substituted or unsubstituted $C_6$-$C_{10}$ aryl groups, and substituted or unsubstituted $C_3$-$C_{10}$ cycloalkyl groups.

The oligomerization process is carried out in a solvent, which is a bicyclic compound or a mixture of bicyclic compounds.

The claimed method provides an increased catalyst activity (up to 78,000 g olefins/one gram of metal per hour) during the oligomerization process and, as a consequence, a reduction in the catalyst unit consumption. Furthermore, the method allows an increase in the efficiency of the process of preparing hexene-1 and octene-1 and a reduction in the formation of a polymer by-product (down to 1% of the total yield of the reaction products).

The inventors of the present invention have found that the use of a solvent, which is a bicyclic compound or a mixture of bicyclic compounds, promotes an increased activity of the catalyst system of oligomerization of $C_2$-$C_4$ olefins and a reduced formation of a polymer by-product. The use of said solvent in the oligomerization process increases the activity of the catalyst used in the oligomerization, and improves its selectivity to the formation of α-olefins, particularly to hexene-1 and octene-1. The bicyclic compound may be decalin (decahydronaphthalene, bicyclo[4.4.0]decane) and its derivatives.

BRIEF DESCRIPTION OF DRAWINGS

FIG. 1 is a PMR spectrum of a PNP ligand for ethylene tetramerization.

DETAILED DESCRIPTION OF THE INVENTION

The present invention relates to a method for preparing α-olefins by oligomerization of $C_2$-$C_4$ olefins in the presence of a catalyst system in a solvent, which is a bicyclic compound or a mixture of bicyclic compounds.

The bicyclic compound used as the solvent may be decalin or derivatives thereof. Decalin may be cis-decalin, trans-decalin or a mixture thereof, in any suitable ratio. Decalin may comprise not more than 30 wt. % of impurities, in particular inert to the catalyst, such as alkyl derivatives of decalin, in particular 1-methyldecalin, 2-methyldecalin, ethyldecalin, propyldecalin, butyldecalin, and other alkyl and isoalkyl derivatives; perhydroindane (bicyclo[4.3.0]nonane), perhydroazulene (bicyclo[5.3.0]decane) and alkyl derivatives thereof, and the like.

The source of the above bicyclic compounds and their derivatives, in particular of decalin, perhydroindane, perhydroazulene, and derivatives thereof, is coal tar and heavy pyrolysis resin. They contain naphthalene, alkylnaphthalenes, indene, and azulene, which can be converted into the corresponding perhydro derivatives by exhaustive hydrogenation on noble metals. Tetrahydronaphthalene (tetralin) is a large-tonnage product of incomplete hydrogenation of naphthalene, used as a solvent for brown coal, and decalin is a by-product of the process of tetralin production.

The present inventors have found for the first time that decalin promotes active oligomerization, namely trimerization and tetramerization, in the presence of MAO.

The claimed method of oligomerization of olefins comprises reaction of alpha-olefin-containing raw materials under oligomerization conditions, in the presence of a catalyst comprising a transition metal source, a P—N—P ligand and an activator, which is alkylaluminoxane. Said reaction runs in decalin.

The claimed method may be used for different processes of oligomerization, including for oligomerization of olefins, for example, for trimerization and tetramerization of $C_2$-$C_4$ olefins, for example, ethylene.

As shown above, the oligomerization process is carried out in the presence of a catalyst comprising a transition metal source, a P—N—P ligand and an activator, which is alkylaluminoxane.

The transition metal may be Ti, Zr, Hf, Ni, Cr, Fe, Co, Pd, Pt, or the like, or a combination thereof. Preferably, the transition metal is chromium (Cr), titanium (Ti), or zirconium (Zr). Most preferably, the transition metal is chromium (Cr).

The transition metal source may be an organic and/or inorganic compound. The oxidation degree of a metal depends on the metal used. In general, the metal source is a compound of the general formula $MeX_n$, wherein Me is a transition metal selected from the group consisting of Ti, Zr, Hf, Ni, Cr, Fe, Co, Pd, Pt, and the like, and a combination thereof, X may be the same or different, and n is an integer from 1 to 6. X may be an organic or inorganic substituent. When X is an organic substituent, it may contain from 1 to 20 carbon atoms and may be alkyl group, alkoxyl group, carboxyl group, acetylacetonate group, amino group, amido group, or the like. Suitable inorganic substituents of X include halides, sulfates, oxides and other of transition metals.

Examples of the transition metal source include, but are not limited to, titanium (III) chloride, titanium (IV) chloride, titanium (IV) butoxide, titanium (IV) isopropoxide, zirconium (IV) chloride, zirconium (IV) oxychloride, zirconium (IV) butoxide, cobalt (II) ethylhexanoate, hafnium (IV) chloride, nickel (II) chloride, iron (III) chloride, cobalt (II) ethylhexanoate, palladium (II) chloride, hydrogen hexachloroplatinate (IV), etc.

When the transition metal is chromium, the chromium source may be an organic and/or inorganic chromium compound. The oxidation degree of chromium in compounds may vary and be equal to 0, +1, +2, +3, +4, +5, and +6. Generally, the chromium source is a compound of the general formula $CrX_n$, wherein X may be the same or different, and n is an integer from 1 to 6. X may be an organic or inorganic substituent. When X is an organic substituent, it may contain from 1 to 20 carbon atoms and may be alkyl group, alkoxyl group, carboxyl group, acetylacetonate group, amino group, amido group, or the like. Suitable inorganic substituents of X include halides, sulfates, chromium oxides, and the like. Examples of the chromium source include chromium (III) chloride, chromium (III) acetate, chromium (III) tris-ethylhexanoate, chromium (III) acetylacetonate, chromium (III) pyrrolide, chromium (II) acetate, chromium (IV) dioxide dichloride ($CrO_2Cl_2$), and the like.

The P—N—P ligand being a component of the catalyst system can be represented by the general formula:

Ar¹Ar²P—N(R)—PAr³Ar⁴, wherein $Ar^{1-4}$ may be the same or different and are substituted or unsubstituted $C_6$-$C_{10}$ aryl groups, such as phenyl, tolyl, ethylphenyl, cumyl, naphthyl, most preferably alkylaryl without an o-substituent, in particular, p-tolyl, m-ethylphenyl, or unsubstituted phenyl;

R is linear or branched $C_1$-$C_4$ alkyl, substituted or unsubstituted $C_6$-$C_{10}$ aryl, substituted or unsubstituted $C_3$-$C_{10}$ cycloalkyl, such as methyl, ethyl, propyl, butyl, isobutyl, benzyl, allyl, most preferably alkyl having one α-branch, for example isopropyl, sec-butyl, cycloalkyl, such as cyclopropyl, cyclobutyl, cyclopentyl, cyclohexyl, cycloheptyl, cyclooctyl, cyclononyl, and the like.

The P—N—P ligand can be prepared by reacting alkylamine and diarylchlorophosphine(s) in the presence of a base.

The activator used for alkylation of the transition metal to form a metal alkyl and a counterion (aluminate) for a cationic transition metal complex is an unmodified alkylaluminoxane. An unmodified methylaluminoxane (aluminoxane) is preferred. It is more preferable to use MAO in the form of a 10% solution in toluene. However, based on data in the literature, the use of other aluminoxanes (ethylaluminoxane, isobutylaluminoxane) is less preferred due to their lower ionizing capacity (D.B. Malpass, Commercially Available Metal Alkyls and Their Use in Polyolefin Catalysts, p. 13 (part 1.5.4), in: Handbook of Transition Metal Polymerization Catalysts Ed. by Ray Hoff and Robert T. Mathers 2010 John Wiley & Sons, Inc.)

The catalyst system comprising a chromium source, a P—N—P ligand and alkylaluminoxane can be prepared by mixing the chromium source and the P—N—P ligand, wherein the mixing is preferably carried out under ultrasonic exposure to homogenize the catalyst system, followed by mixing the resulting mixture with alkylaluminoxane. The organometallic catalyst may be homogeneous or heterogeneous.

The ratio of the components of the catalyst system may vary. The molar ratio of transition metal:PNP ligand:aluminum can be 1:0.1-10:10-5000, preferably 1:0.5-2:100-1000, more preferably 1:0.6-1.5:200-500.

The mixing of the metal source and the P—N—P ligand can be carried out in solvents dissolving both the metal source, in particular chromium, and the ligand. Said solvents may be both aromatic and aliphatic, as well as cycloaliphatic solvents, including benzene, toluene, ethylbenzene, xylene, mesitylene, cumene, and other aromatic solvents; however, it is more preferable to use toluene or ethylbenzene since the catalyst prepared by using these solvents, exhibit greater stability.

The organometallic catalyst prepared by the above-indicated method is preferably stored at a low temperature, preferably not higher than minus 78° C., to prolong its storage life.

The catalyst concentration in said solvents is from 1 to 15 mol/L, preferably from 3 to 10 mol/L, more preferably from 5 to 8 mol/L.

The catalyst system obtained by the above-described method, before being fed to the oligomerization reactor, is mixed with a solvent, which is a bicyclic compound or a mixture of bicyclic compounds, for example decalin, in a weight ratio of organometallic catalyst:solvent of from 1:100 to 1:10000, preferably from 1:150 to 1:5000, most preferably from 1:200 to 1:2000.

Along with the above-indicated components of the catalyst system, the oligomerization process can further involve one or more zinc compounds. They may be added to the catalyst system directly at the step of preparing the system or separately to an oligomerization reactor. The zinc compound may be used as an activator of the catalytic center, in particular chromium. The zinc compound may be zinc (Zn (0)), alkylzinc, in particular dialkylzinc, for example dimethylzinc, diethylzinc, dibutylzinc; arylzinc, for example, diphenylzinc, ditolylzinc; zinc amides, for example zinc pyrrolide or zinc-porphyrin complexes, for example zinc-5,10,15,20-tetraphenylporphyrin, zinc oxygenates, for example, zinc formate, zinc acetate, zinc 2-ethylhexanoate; zinc halides, for example, anhydrous zinc chloride; or a combination thereof. It is preferred to use zinc compounds soluble in the solvents used in the oligomerization process, in particular, in decalin. The zinc compound may be used in the form of a solution.

The ratio of the components in the catalyst system, including the zinc compound, may vary. The molar ratio of aluminum:transition metal may be from 10:1 to 5000:1, from 100:1 to 1000:1, most preferably from 200:1 to 500:1. The molar ratio of ligand:transition metal may vary from 2:1 to 1:2, preferably from 1.5:1 to 1:1.5. The molar ratio of zinc:transition metal may vary and ranges from 2:1 to 1000:1, preferably 20:1 to 200:1.

The time between the preparation of the catalyst system and the feeding thereof to the reactor should not exceed 60 minutes, preferably 20 minutes, most preferably 5 min. It is preferred to limit the time between the preparation of the catalyst system and the feeding thereof to the reactor, thereby minimizing the formation of a large amount of a polymer.

The raw materials for preparing α-olefins may be olefins, such as ethylene (ethene), propylene (propene), and butene (butene). In a preferred embodiment, the starting olefin is ethylene.

The oligomerization process of olefins is carried out to obtain higher olefins. Industrially important processes are processes for preparing alpha-olefins (α-olefins). α-Olefins are compounds with a carbon-carbon double bond (C═C) at the alpha position. α-Olefins prepared in the oligomerization process can include various $C_5$-$C_{40}$ olefins and a mixture thereof. For example, α-olefins prepared in the oligomerization process may be pentene-1, hexene-1, heptene-1, octene-1, nonene-1, decene-1, undecene-1, dodecene-1, higher α-olefins, or a mixture thereof. Preferably, the oligomerization process is a process of tri- and/or tetramerization of ethylene to form hexene-1 and/or octene-1.

The claimed method for preparing α-olefins by oligomerization of $C_2$-$C_4$ olefins is carried out in any reactor known in the art. The catalyst system mixed with a solvent, which is a bicyclic compound or a mixture of bicyclic compounds, in particular decalin, is fed to the reactor. The reactor is then filled with $C_2$-$C_4$ olefins and optionally with hydrogen as a diluent, and then the oligomerization process is carried out to obtain α-olefins.

The oligomerization process may be carried out in any reactor known in the art. Suitable reactors include a continuous reactor with a stirrer, a batch reactor, a plug-flow reactor, and a tubular reactor. The reactor may be a gas-liquid reactor, for example, an autoclave with a stirrer, a bubble column (bubble reactor) with co- or countercurrent gas and liquid flows, or a bubbling gas-lift reactor.

In a preferred embodiment of the method, when the oligomerization process is trimerization and tetramerization of $C_2$-$C_4$ olefins, in particular ethylene, to produce hexene-1 and octene-1, a pressure of $C_2$-$C_4$ olefins may vary from 1 to 200 bar, preferably from 5 to 100 bar, most preferably from 20 to 60 bar. It is preferred to elevate the pressure to increase the rate of oligomerization.

The temperature of the oligomerization process may range from 0 to 160° C., preferably from 30 to 120° C. It is most preferred to maintain the temperature in the reactor between 40 and 80° C. At this temperature a polymer by-product, in particular polyethylene, is precipitated from the solution and discharged from the reactor in the form of slurry, and the catalyst system is the most active and selective. The oligomerization process at a higher temperature (above 80° C.) can lead to deactivation of the catalyst system.

In accordance with the claimed method, the reaction time may vary. The reaction time may be defined as a residence time of raw materials and a solvent in the oligomerization reaction zone. In the case of a continuous flow reactor, the reaction time can be defined as an average residence time. The reaction time may vary depending on olefins used as raw materials, a reaction temperature, pressure and other process parameters. In embodiments of the method, the reaction time does not exceed 1 day. The reaction time may be less than 12 hours, less than 6 hours, less than 3 hours, less than 2 hours, less than 1 hour, less than 30 minutes, less than 15 minutes, less than 10 minutes, less than 5 minutes, less than 3 minutes, less than 2 minutes, less than 1 minute, less than 30 sec, less than 15 sec, less than 10 sec, less than 5 sec, less than 3 sec, and less than 1 sec. The reaction time of from 30 min to 60 min is most preferred.

According to the claimed method, the olefin and the catalyst system can contact with hydrogen that is fed to the oligomerization reactor and is used as a diluent. Hydrogen can accelerate the oligomerization reaction and/or increase the activity of the organometallic catalyst. Further, hydrogen can reduce the amount of the formed polymer by-product and limit its deposition on the walls of the equipment.

The solvent in the oligomerization process is a bicyclic compound, namely decahydronaphthalene (decalin). Decalin purified from tetralin impurities with the content of aromatic compounds of not more than 2 wt. % is preferred. Decalin may be a mixture of cis- and trans-decalin in various ratios. The weight ratio of the cis- and trans-decalin may range from 1:99 to 99:1, preferably from 2:98 to 98:2, most preferably from 3:97 to 50:50.

Decalin can be purified from tetralin impurities by the treatment with sulfuric acid according to the method disclosed, for example, in application US 2007/0156003.

The oligomerization process of olefins is carried out in the absence of water and oxygen. The presence of water and oxygen can cause hydrolysis and oxidation of low-oxidation state organometallic compounds, resulting in complete or partial deactivation of the catalyst.

According to the claimed method, the effluent from the reactor may contain the organometallic catalyst, a variety of products, by-products, the solvent, and polymers formed during oligomerization.

The effluent from the reactor can be treated with a deactivation agent. Suitable deactivation agents known in the art include water, alcohols, amines, amino alcohols, and a mixture thereof. The alcohols include methanol, ethanol, n-propanol, isopropanol, n-butanol, isobutanol, tert-butanol, 2-ethylhexanol, and a mixture thereof. Examples of suitable amines include ammonia, methylamine, dimethylamine, trimethylamine, ethylamine, diethylamine, triethylamine, tri-n-propylamine, diisopropylethylamine, tri-n-butylamine, piperazine, pyridine, ethylenediamine, diethylenetriamine, and a mixture thereof. Examples of aminoalcohols include ethanolamine, diethanolamine, triethanolamine, methyldiethanolamine, dodecyldiethanolamine, 1-amino-2-propanol, and a mixture thereof. According to the claimed method, the deactivation agent can be water.

The effluent from the reactor optionally can be cooled by passing thereof, for example, through a heat exchanger. The cooling of the effluent from the reactor may include mixing the hot effluent from the reactor with a cooled effluent. The cooling of the effluent from the reactor is carried out to a temperature of from 100° C. to 20° C., preferably to a temperature of less than 95° C., less than 90° C., less than 85° C., less than 80° C., less than 75° C., less than 70° C., less than 65° C., less than 60° C., less than 55° C., less than 50° C., less than 45° C., less than 40° C., less than 35° C., less than 30° C., or less than 25° C. The effluent from the reactor may be cooled to ambient temperature, for example, from 20 to 25° C. The temperature to which the effluent from the reactor is cooled is so as to allow the control of the polymer precipitation from the solvent. Thus, the effluent from the reactor can be cooled in a decanter, from which polyolefin slurry is periodically discharged.

This method allows a significant increase in the catalyst activity (up to 78,000 g of olefins/one g of metal per hour) during the oligomerization process and, as a consequence, reduces the catalyst unit consumption. When the system capacity, in terms of olefins, is 1000 kg/h, the catalyst consumption is 12 to 27.8 g/h based on transition metal. Furthermore, the method allows an increase in the efficiency of the process of preparing hexene-1 and octene-1 and a reduction in the formation of a polymer by-product (down to 1% of the total yield of the reaction products).

The invention is further illustrated by the following examples.

The used raw materials were methylaluminoxane (a 10% solution in toluene), phosgene (a 10% solution in toluene), chromium (III) acetylacetonate (Aldrich), cyclohexylamine, and diphenylphosphine (Acros Organics).

The PNP-ligand (PMR spectrum is presented in FIG. 1) was synthesized from cyclohexylamine and diphenylchlorophosphine by the procedure described in [Cooley N. A., Green S. M., and Wass D. F. Nickel Ethylene Polymerization Catalysts Based on Phosphorus Ligands//Organometallics 2001, Vol. 20, P. 4769-4771].

Diphenylchlorophosphine was prepared from diphenylphosphine and phosgene as disclosed in [Henderson W. A. Jr., Buckler S. A., Day N. E., Grayson M. Preparation of Alkyl Chlorophosphines//J. Org. Chem. 1961. Vol. 26. P.4770-4771], Example 1. Synthesis of a PNP-Ligand Diphenylchlorophosphine (8.5 g, 38.6 mmol, 2 eq.) was fed into a flask with a solution of cyclohexylamine (1.9 g, 19.3 mmol, 1 eq.) and triethylamine (3.9 g, 38.5 mmol, 2 eq.) in 100 mL of dichloroethane under a nitrogen atmosphere. The reaction mixture was stirred for 20 hours at room temperature. Water in an amount of 50 ml was added, stirred, and the organic layer (solution in dichloroethane) was separated in a separating funnel and then filtered through Celite 500. After that, the solvent was evaporated, 30 ml of methanol was added to the resulting honey-like mass and cooled until white crystals are precipitated. The precipitate was filtered off and dried at room temperature under vacuum. The resulting compound is a white crystalline solid (3.7 g). $^{31}$P NMR analysis: 50.7 ppm, br.; $^1$H NMR, see FIG. 1.

Example 2. Oligomerization with MAO in Decalin

The PNP-ligand (179.8 mg, 0.385 mmol) and chromium (III) acetylacetonate (67.1 mg, 0.192 mmol) were mixed in toluene (5 ml) under ultrasonic exposure. MAO in toluene (25.5 mL, 38.5 mmol) was added, and immediately after mixing, the blue-green solution was used as a source of the active catalyst. The catalyst in an amount of 3 ml was taken and mixed with 150 ml of dry decalin in a nitrogen box.

The resulting mixture was transferred to an evacuated 250 ml Parr reactor by a differential pressure at 50° C. Hydrogen (1 atm) was fed to the reactor, and its content was thermostated under stirring (800 rpm) due to the circulation of the coolant inside the jacket of the reactor to stabilize temperature within a range of 57 to 62° C. Then, ethylene was continuously dosed to the reactor to the total pressure of up to 31 bar, and the dosing was continued at a constant pressure as the gas was depleted (60-70° C.), under stirring the reaction mass. After 30-60 min, the dosing of ethylene was stopped, the mixture was cooled to 40° C. and degassed, and the reaction mixture was discharged through a lower ball valve. The liquid phase was analyzed (GC, GC-MS).

The results of the experiment are given in Table 1.

Example 3. Oligomerization with MAO in Decalin Purified from Tetralin Impurities The process was carried out as described in Example 2, except that the duration of the process was 15 minutes, and the solvent was decalin purified from tetralin impurities.

Decalin was purified as follows.

Technical decalin (1.5 L) containing impurities of ethylbenzene (0.5%), butylbenzene (0.5%), indane (0.5%), and tetralin (6%) was mixed with a high-grade sulfuric acid (96% solution, 1 L) and stirred vigorously at room temperature for 24 hours. After that, the stirring was stopped, and the resulting mixture was allowed to separate. The upper layer was separated, washed in a separatory funnel with 500 mL of a 10% aqueous solution of sodium hydrogencarbonate 2 times and with distilled water to pH 6-7. Then, the organic phase was dried over sodium sulfate and distilled over molten sodium.

The results of the experiment are given in Table 1.

Example 4. Oligomerization with MAO in Decalin Purified from Tetralin Impurities with a Reduced Toluene Content The decalin used in this example was purified according to the procedure described in Example 3.

The PNP-ligand (179.8 mg, 0.385 mmol) and chromium (III) acetylacetonate (67.1 mg, 0.192 mmol) were mixed in toluene (5 ml) under ultrasonic exposure. MAO in toluene (25.5 mL, 38.5 mmol) and then decalin (20 mL) were added, and 20 mL of toluene was distilled off under vacuum. The blue-green solution was used as a source of the active catalyst. The catalyst in an amount of 3 mL was taken and mixed with 150 ml of dry decalin in a nitrogen box.

The oligomerization process was carried out as described in Example 2.

The results of the experiment are given in Table 1.

Example 5. Oligomerization with MAO in Toluene (Comparative Experiment According to Example 2 of the Prototype WO2004/056479)

The process was carried out as described in Example 2 according to WO2004/056479, except that the used solvent was toluene, and the ligand was a compound of the formula: (phenyl)2P—N(cyclohexyl)-P(phenyl)2.

A solution of 29.0 mg of the P—N—P ligand (0.073 mmol) in 5 mL of toluene was fed into a Schlenk flask containing 12.4 ml of a solution of CrCl3 (tetrahydrofuran)3 (0.033 mmol) in 15 mL of toluene. The resulting solution was stirred for 5 minutes at room temperature and transferred to a 250 ml Parr reactor containing a mixture of toluene and MAO (9.9 mmol), at 80° C. Then ethylene was dosed to the reactor. The temperature in the reactor was maintained at 85° C., and the pressure of ethylene was maintained at 30 bar. The reaction mass was stirred at 1100 rpm. After 60 minutes, the dosing of ethylene was stopped, and the reaction mass was cooled to 40° C. and degassed. The reaction mass was treated with a deactivation agent, which was ethanol and a 10% aqueous solution of hydrochloric acid (HCl). A sample of the resulting mixture was dried over anhydrous sodium sulfate and analyzed by gas chromatography (GC). In the assay, heptane was used as an internal standard.

The results of the experiment are given in Table 1.

Example 6. Oligomerization with MAO in Cyclohexane (Comparative Experiment According to Example 22 of the Prototype WO2004/056479)

The process was carried out as described in Example 22 according to WO2004/056479, except that the chromium (III) acetylacetonate was introduced into the reaction system in the form of a solution in toluene since it is insoluble in cyclohexane. The used ligand was a compound of the formula: (phenyl)$_2$P—N(cyclohexyl)-P(phenyl)$_2$.

5.8 mg of a solution of the P—N—P ligand (0.014 mmol) obtained in Example 1 in 10 ml of cyclohexane was fed into a Schlenk flask comprising a solution of 3.5 mg of chromium (III) acetylacetonate (0.01 mmol) in 10 mL of toluene. The resulting solution was stirred for 5 minutes at room temperature. Then, the solution and a 7% solution of MAO (2 mmol) in toluene were added by a differential pressure to a 250 ml Parr reactor containing cyclohexane (170 ml), at 45° C. Then ethylene was dosed to the reactor. The temperature in the reactor was maintained at 45° C., the pressure of ethylene was maintained at 45 bar, under stirring the reaction mass. After 39 minutes, the dosing of ethylene was stopped, and the reaction mass was cooled to 40° C. and degassed. The reaction mass was treated with a deactivation agent, which was ethanol and a 10% aqueous solution of hydrochloric acid (HCl). A sample of the resulting mixture was dried over anhydrous sodium sulfate and analyzed by gas chromatography (GC). In the assay, heptane was used as an internal standard.

The results of the experiment are given in Table 1.

Example 7. Oligomerization with MAO in the Presence of Diethylzinc in Decalin Purified from Tetralin Impurities The PNP-ligand (89.9 mg, 0.192 mmol) and chromium (III) acetylacetonate (67.1 mg, 0.192 mmol) were mixed in toluene (5 ml) under ultrasonic exposure. MAO in toluene (40 mL, 60.4 mmol) was added, and immediately after mixing, the blue-green solution was used as a source of the active catalyst. The catalyst in an amount of 3 mL was taken and mixed with 150 mL of a dry solvent (decalin), and a 1M solution of diethylzinc in hexane (0.38 mL, 0.38 mmol) was added in a nitrogen box.

Then the mixture was transferred to an evacuated 250 ml Parr reactor by a differential pressure at 45° C. Hydrogen (1 atm) was dosed to the reactor, and its content was thermostated under stirring (800 rpm) due to the circulation of the coolant inside the jacket of the reactor to stabilize temperature within a range of 43 to 47° C. Then, ethylene was continuously dosed to the reactor to the total pressure of up to 41 bar, and the dosing was continued at a constant pressure as the gas was depleted (45-50° C.), under stirring the reaction mass. After 30 min, the dosing of ethylene was stopped, the mixture was cooled to 30° C. and degassed, and the reaction mixture was discharged through a lower ball valve. The liquid phase was analyzed (GC).

Decalin was purified according to the procedure disclosed in Example 3.

The results of the experiment are given in Table 1.

Example 8. Oligomerization with MAO in Decalin Purified from Tetralin Impurities, Using a Catalyst System with a 2-Hour Storage Time The process was carried out as described in Example 2 except that the catalyst system was kept under nitrogen atmosphere for 2 hours before mixing with the solvent.

The results of the experiment are given in Table 1.

Example 9. Synthesis of Butylindene

Butyllithium (2.5 M, 300 ml) was added to a solution of indene (87 g, 0.75 mol) in THF (216 g) and cyclohexane (400 g) under ice-cooling for 2 hours, warmed to room temperature over 1 h, then a solution of butylbromide (102.8 g, 0.75 mol) in cyclohexane (100 g) was added for 15 min, heated for 3 hours at 50° C., and then stirred for 16 hours at 25° C. A saturated NaCl solution (200 mL) was then added to the mixture and shaken in a separatory funnel, the organic layer was separated, washed with water (200 ml), then again the saturated NaCl solution (200 ml of) was added, and was dried over sodium sulfate. The organic layer was evaporated in a rotary evaporator at 300 mbar/65° C., the residue was distilled under vacuum, and the main fraction with a boiling point of 120-130° C./20 mbar was collected. The yield was 77 g, purity was 79%, and the impurities (GC-MS) were dibutylindenes.

Example 10. 1-Butyl-perhydroindane in Decalin. Mixture of Isomers

The product of Example 9 was mixed with a purified decalin (100 g) and hydrogenated at 250-270° C. and 100-120 bar on a 5% Pt-10% Pd—C catalyst (10 g) for 72 hours. The resulting product comprised less than 2% of aromatic compounds (GC-MS). The catalyst was filtered off, washed with 50 ml of decalin, the mixed solvent was subjected to purification with sulfuric acid as described above in Example 3, and then the mixture was distilled over sodium under vacuum. The mixture contained four diastereomeric pairs of butyl-perhydroindanes in an amount of: 5.4%; 10.0%; 1.1%; and 3.6%, in the decalin solution (the total amount of decalin—74% PID area).

Example 11. Perhydroindane

Indene (250 ml) was hydrogenated at 250-270° C. and 100-120 bar on a 5% Pt-10% Pd—C catalyst (10 g) for 72 hours. The purity of the obtained product was 97% (a mixture of cis- (69.2%) and trans- (26.1%) isomers). The product was subjected to purification with sulfuric acid and distilled similarly to decalin and butylperhydroindane.

Example 12. Oligomerization in Mixed Solvents

The PNP-ligand (89.9 mg, 0.192 mmol) and chromium (III) acetylacetonate (67.1 mg, 0.192 mmol) were mixed in ethylbenzene (4 ml) under ultrasonic exposure. MAO in toluene (25.5 mL, 38.5 mmol) and diethylzinc (0.4 mL) was added, and immediately after mixing, the blue-green solution was used as a source of the active catalyst. The catalyst in an amount of 3 mL (corresponds to 1 mg of chromium) was taken and mixed with 150 mL of the dry solvent in a nitrogen box. The remaining part of the catalyst solution was frozen at (−196) ° C., and unfreezed to 0° C. immediately before the synthesis.

The resulting mixture was transferred to an evacuated 250 ml Parr reactor by a differential pressure at 50° C. Hydrogen (1 atm) was dosed to the reactor, and its content was thermostated under stirring (800 rpm) due to the circulation of the coolant inside the jacket of the reactor to stabilize temperature within a range of 57 to 62° C. Then, ethylene was continuously dosed to the reactor to the total pressure of up to 31 bar, and the dosing was continued at a constant pressure as the gas was depleted (60-70° C.), under stirring the reaction mass. After 30-60 min, the dosing of ethylene was stopped, and the reaction mixture was discharged, while being degassed, through a lower ball valve. Silicagel in an amount of 5 g was added and kept for 30 minutes. The liquid phase was analyzed (GC, GC-MS).

The results of the experiments are shown in Table 2 (Examples 12.1-12.4).

TABLE 1

Results of the experiments on ethylene oligomerization

| Example | Solvent | Toluene content, % | Tetralin content, % | Catalyst activity, olefin (g)/ chromium (g), per hour | Calculated catalyst consumption, chromium (g)/olefin (t), per hour | $C_6$-1 yield, g | Purity, $C_6$, % | $C_8$-1 yield, g | Purity, $C_8$, % | $C_6$-1 + $C_8$-1 selectivity, % | $C_8$/ $C_6$ | Polymer, g |
|---|---|---|---|---|---|---|---|---|---|---|---|---|
| 2 | Decalin | 1.4 | 6.0 | 5700 | 175 | 0.84 | 73.0 | 2.55 | 98.3 | 59 | 3.0 | 0.3 |
| 3 | Decalin | 1.8 | 0.04 | 36000 | 27.8 | 1.8 | 83.5 | 4.05 | 99.3 | 65 | 2.3 | 0.08 |

TABLE 1-continued

Results of the experiments on ethylene oligomerization

| Example | Solvent | Toluene content, % | Tetralin content, % | Catalyst activity, olefin (g)/ chromium (g), per hour | Calculated catalyst consumption, chromium (g)/olefin (t), per hour | $C_6$-1 yield, g | Purity, $C_6$, % | $C_8$-1 yield, g | Purity, $C_8$, % | $C_6$-1 + $C_8$-1 selectivity, % | $C_8/C_6$ | Polymer, g |
|---|---|---|---|---|---|---|---|---|---|---|---|---|
| 4 | Decalin | 0.5 | 0.04 | 42000 | 23.8 | 4.0 | 80.5 | 12.0 | 99.3 | 75 | 3.0 | 0.2 |
| 5 (comparative, according to the prototype) | Toluene | — | — | 2300 | 435 | 0.46 | 83.2 | 1.38 | 97.0 | 80 | 3.0 | 0.3 |
| 6 (comparative, according to the prototype) | Cyclohexane | 6.5 | — | 600 | 1670 | 0.29 | 68.6 | 0.34 | 91.5 | ND | 1.2 | 0.5 |
| 7 (with ZnEt$_2$) | Decalin | 1.8 | 0.04 | 78000 | 12.8 | 2.86 | 83.0 | 9.2 | 99.5 | 85 | 3.2 | 0.15 |
| 8 (catalytic system with 2-hour storage time | Decalin | 1.8 | 0.04 | 6000 | 167 | 0.88 | 78.0 | 2.68 | 99.0 | ND | 3.0 | 12.0 |

TABLE 2

Results of the experiments on ethylene oligomerization in bicyclic solvents

| Example | Reaction time, min | Solvent Perhydroindane, % | Decalin, % | Butyl perhydroindane, % | Content of aromatic compounds, % | Activity, olefin (g)/chromium (g), per hour | C6-1 yield, g | C8-1 yield, g | C8-1 purity, % | C8/C6 |
|---|---|---|---|---|---|---|---|---|---|---|
| 12.1 | 60 | 18.8 | 70.7 | 0 | 1.9 | 7500 | 1.72 | 6.16 | 97.7 | 3.6 |
| 12.2 | 45 | 83.0 | 10.6 | 0 | 3.3 | 1100 | 0.25 | 0.61 | 92.0 | 2.4 |
| 12.3 | 60 | 14.3 | 61.6 | 17.2 | 2.3 | 1100 | 0.35 | 0.84 | 94.0 | 2.4 |
| 12.4 | 40 | 4.5 | 70.7 | 4.3 | 4.1 | 12500 | 5.03 | 11.07 | 98.4 | 2.2 |

The results of the experiments show the advantage of using decalin as a solvent in the oligomerization process. As can be seen from Table 1, the activity of the catalyst system during the oligomerization process in decalin reaches 42,000 g of olefins per 1 g of chromium per hour (Table 1, Example 4), whereas the activity of the catalyst system during the oligomerization process in cyclohexane or toluene reaches only 600 and 2,300 g of olefins per 1 g of chromium per hour, respectively (Examples 5 and 6). The addition of alkylzinc also has a positive effect on the activity of the catalyst system (Example 7, Table 1). In such a case, the activity of the catalyst system reaches 78,000 g of olefins per 1 g of chromium per hour.

A reduction in the catalyst consumption also should be noted. When the system capacity, in terms of olefins, is 1000 kg/h, the consumption of the catalyst is not more than 12.8 to 27.8 g/h based on elemental chromium.

It should be also noted that when the oligomerization process is carried out in decalin, the formation of by-products reduces to 0.08 g (Example 3, Table 1). In addition, as can be seen from the obtained data, when the content of decalin in the solvent is less than 70 wt. %, the activity of the catalyst and the yield of the product drop sharply (Table 2, Examples 12.2 and 12.3); therefore, as the content of decalin in the solvent increases and the content of impurities in the solvent decreases, the activity of the catalyst increases (Table 1, Examples 2, 3, and 4).

Thus, it can be concluded that the use of a bicyclic compound or a mixture of bicyclic compounds, in particular decalin, results in an increased catalyst activity, and a reduced formation of a polymer by-product.

The invention claimed is:

1. A method for preparing α-olefins by oligomerization of $C_2$-$C_4$ olefins in the presence of a catalyst system comprising a transition metal source, an activator, which is an alkylaluminoxane, and a compound of formula (I),

$$Ar^1Ar^2P-N(R)-PAr^3Ar^4 \quad \text{[formula I]},$$

wherein
$Ar^{1-4}$ are the same or different and selected from substituted or unsubstituted $C_6$-$C_{10}$ aryl groups;
R is selected from linear or branched $C_1$-$C_4$ alkyl group, substituted or unsubstituted $C_6$-$C_{10}$ aryl group, and substituted or unsubstituted $C_3$-$C_{10}$ cycloalkyl group;
wherein the oligomerization process is carried out in a solvent, which is a bicyclic compound or a mixture of bicyclic compounds.

2. The method of claim 1, wherein the oligomerization is trimerization or tetramerization.

3. The method of claim 1, wherein $C_2$-$C_4$ olefin is ethylene.

4. The method of claim 1, wherein the transition metal is selected from the group comprising Ti, Zr, Hf, Ni, Cr, Fe, Co, Pd, Pt, and a combination thereof, preferably Cr.

5. The method of claim 1, wherein the transition metal source is a compound of the formula: $MeX_n$, wherein Me is a transition metal selected from the group comprising Ti, Zr, Hf, Ni, Cr, Fe, Co, Pd, Pt, and a combination thereof, X is an organic or inorganic substituent, the same or different, and n is an integer from 1 to 6.

6. The method of claim 5, wherein X is an organic substituent having 1 to 20 carbon atoms and is selected from the group comprising alkyl, alkoxyl, carboxyl, acetylacetonate, amino, amido, and a combination thereof.

7. The method of claim 5, wherein X is an inorganic substituent and is selected from the group comprising halides, sulfates, and oxides of transition metals.

8. The method of claim 5, wherein the transition metal source is a Cr compound of the formula: $CrX_n$, selected from the group comprising chromium (III) chloride, chromium (III) acetate, chromium (III) tris-ethylhexanoate, chromium (III) acetylacetonate, chromium (III) pyrrolide, chromium (II) acetate, or chromium (IV) dioxide dichloride.

9. The method of claim 1, wherein alkylaluminoxane is methylaluminoxane.

10. The method of claim 1, wherein the bicyclic compound is decalin (decahydronaphthaline).

11. The method of claim 10, wherein decalin may be cis-decalin, trans-decalin, or a mixture thereof.

12. The method of claim 10 or claim 11, wherein decalin comprises not more than 30 wt. % of impurities.

13. The method of claim 1, wherein the catalyst system further comprises a zinc compound.

14. The method of claim 13, wherein the zinc compound is selected from the group comprising alkylzinc compounds, arylzinc compounds, zinc amides, zinc oxygenates, zinc halides, and a combination thereof.

15. The method of claim 13, wherein the zinc compound is zinc metal (Zn).

16. The method of claim 14, wherein the zinc compound is diethylzinc.

17. The method of claim 1, wherein $Ar^{1-4}$ are alkylaryl selected from the group comprising phenyl, tolyl, ethylphenyl, cumyl, and naphthyl.

18. The method of claim 1, wherein R is a radical selected from the group comprising methyl, ethyl, propyl, butyl, isobutyl, benzyl, allyl, cyclopropyl, cyclobutyl, cyclopentyl, cyclohexyl, cycloheptyl, cyclooctyl, and cyclononyl.

19. The method of claim 1, wherein the catalyst system is prepared by mixing the transition metal source and a compound of formula (I), wherein the mixing is carried out under ultrasonic exposure to prepare a homogenous mixture, followed by mixing the prepared mixture with alkylaluminoxane.

20. The method of claim 1, wherein the catalyst system is homogenous or heterogeneous.

21. The method of claim 19, wherein the mixing of the transition metal source and a compound of formula (I) is carried out in a solvent selected from the group comprising benzene, toluene, ethylbenzene, xylene, mesitylene, and cumene, preferably toluene and ethylbenzene.

22. The method of claim 19, further comprising adding a zinc compound when preparing the catalyst system.

23. The method of claim 1, wherein a ratio of aluminum: transition metal in the catalyst system is from 10:1 to 5000:1, preferably from 100:1 to 1000:1, most preferably from 200:1 to 500:1.

24. The method of claim 1, wherein a ratio of compound of formula (I):transition metal in the catalyst system is from 2:1 to 1:2, preferably from 1.5:1 to 1:1.5.

25. The method of claim 13, wherein a ratio of zinc: transition metal in the catalyst system is from 2:1 to 1000:1, preferably from 20:1 to 200:1.

26. The method of claim 1, comprising:
mixing the catalyst system with a solvent, which is a bicyclic compound or a mixture of bicyclic compounds;
feeding the resulting mixture to an oligomerization reactor; and
feeding $C_2$-$C_4$ olefins to the oligomerization reactor and carrying out the oligomerization to prepare α-olefins.

27. The method of claim 26, wherein the oligomerization reactor is selected from the group comprising a continuous reactor with a stirrer, a batch reactor, a plug-flow reactor, and a tubular reactor.

28. The method of claim 26, wherein the catalyst system is added for not more than 60 minutes, preferably 20 minutes, most preferably 5 minutes, after preparing thereof.

29. The method of claim 26, wherein the oligomerization is carried out at a temperature of from 0 to 160° C., preferably from 30 to 120° C., most preferably from 40 to 80° C.

30. The method of claim 26, wherein the time of oligomerization in the reactor is from 30 to 60 minutes.

31. The method of claim 26, further comprising feeding gaseous hydrogen.

32. The method of claim 10, wherein the content of aromatic hydrocarbons in decalin is not more than 2 wt. %.

33. The method of claim 10, wherein decalin is substantially free of tetralin.

34. The method of claim 1, wherein the prepared α-olefins comprise $C_5$-$C_{40}$ α-olefins.

35. The method of claim 34, wherein α-olefins preferably contain hexene-1 and octene-1.

36. The method of claim 26, further comprising a step of cooling an effluent from the reactor to a temperature of from 100° C. to 20° C., preferably to a temperature of less than 95° C., less than 90° C., less than 85° C., less than 80° C., less than 75° C., less than 70° C., less than 65° C., less than 60° C., less than 55° C., less than 50° C., less than 45° C., less than 40° C., less than 35° C., less than 30° C., and less than 25° C.

37. The method of claim 36, wherein the effluent from the reactor is cooled to a temperature of from 20 to 25° C.

38. The method of claim 26, further comprising a step of treating the effluent from the reactor with a deactivation agent selected from the group comprising water, alcohols, amines, aminoalcohols, and a mixture thereof.

39. The method of claim 38, wherein the deactivation agent is selected from the group comprising methanol, ethanol, n-propanol, isopropanol, n-butanol, isobutanol, tert-butanol, 2-ethylhexanol, and a mixture thereof.

40. The method of claim 38, wherein the deactivation agent is selected from the group comprising ammonia, methylamine, dimethylamine, trimethylamine, ethylamine, diethylamine, triethylamine, tri-n-propylamine, diisopropylethylamine, tri-n-butylamine, piperazine, pyridine, ethylenediamine, diethylenetriamine, and a mixture thereof.

41. The method of claim 38, wherein the deactivation agent is selected from the group comprising ethanolamine, diethanolamine, triethanolamine, methyldiethanolamine, dodecyldiethanolamine, 1-amino-2-propanol, and a mixture thereof.

* * * * *